(12) United States Patent
Horlacher et al.

(10) Patent No.: US 9,144,545 B2
(45) Date of Patent: Sep. 29, 2015

(54) STEROL ESTER POWDER

(75) Inventors: Peter Horlacher, Bellenberg (DE); Jürgen Gierke, Illertissen/Betlinshausen (DE); Franz Timmermann, Illertissen (DE); Wolfgang Albiez, Illertissen (DE); Alois Hofmann, Illertissen (DE)

(73) Assignee: Cognis IP Management GmbH, Duesseldorf (DE)

( * ) Notice: Subject to any disclaimer, the term of this patent is extended or adjusted under 35 U.S.C. 154(b) by 1466 days.

(21) Appl. No.: 12/064,651

(22) PCT Filed: Aug. 12, 2006

(86) PCT No.: PCT/EP2006/007997
§ 371 (c)(1),
(2), (4) Date: Feb. 25, 2008

(87) PCT Pub. No.: WO2007/022890
PCT Pub. Date: Mar. 1, 2007

(65) Prior Publication Data
US 2008/0187643 A1 Aug. 7, 2008

(30) Foreign Application Priority Data
Aug. 23, 2005 (DE) .......... 10 2005 039 836

(51) Int. Cl.
*A23C 9/18* (2006.01)
*A61K 9/16* (2006.01)
*A23L 1/30* (2006.01)
*A23L 1/305* (2006.01)

(52) U.S. Cl.
CPC .......... *A61K 9/1658* (2013.01); *A23L 1/3004* (2013.01); *A23L 1/305* (2013.01); *A23L 1/3056* (2013.01); *A61K 9/1623* (2013.01)

(58) Field of Classification Search
USPC .......... 426/601, 639, 658, 590, 656, 614
See application file for complete search history.

(56) References Cited

U.S. PATENT DOCUMENTS

| 3,881,005 | A | | 4/1975 | Thakkar et al. |
| 4,376,072 | A | | 3/1983 | Connolly |
| 5,015,483 | A | * | 5/1991 | Haynes et al. .......... 426/73 |
| 5,139,803 | A | * | 8/1992 | Haynes et al. .......... 426/330.6 |
| 5,234,702 | A | * | 8/1993 | Katz et al. .......... 426/72 |
| 5,502,045 | A | | 3/1996 | Miettinen et al. |
| 6,113,972 | A | | 9/2000 | Corliss et al. |
| 6,129,944 | A | * | 10/2000 | Tiainen et al. .......... 426/577 |
| 6,376,482 | B2 | | 4/2002 | Akashe et al. |
| 6,576,285 | B1 | * | 6/2003 | Bader et al. .......... 426/590 |
| 6,623,780 | B1 | | 9/2003 | Stevens et al. |
| 6,627,245 | B1 | | 9/2003 | Doat et al. |
| 6,677,327 | B1 | * | 1/2004 | Gottemoller .......... 426/590 |
| 2002/0048606 | A1 | | 4/2002 | Zawistowski |
| 2003/0165572 | A1 | | 9/2003 | Auriou |
| 2004/0209953 | A1 | * | 10/2004 | Wai Lee .......... 514/547 |
| 2006/0034934 | A1 | | 2/2006 | DeGuise et al. |
| 2006/0035009 | A1 | | 2/2006 | Gaonkar et al. |
| 2006/0035871 | A1 | | 2/2006 | Auweter et al. |
| 2007/0154557 | A1 | * | 7/2007 | Veldhuizen et al. .......... 424/488 |
| 2009/0047392 | A1 | | 2/2009 | Horlacher et al. |

FOREIGN PATENT DOCUMENTS

| DE | 102 53 111 A1 | 5/2004 |
| DE | 10200601663 | 9/2007 |
| EP | 0 669 835 B1 | 11/1998 |
| EP | 1148793 | 10/2001 |
| EP | 1 059 851 B1 | 5/2002 |
| EP | 1 003 388 B1 | 8/2002 |
| EP | 0 897 671 B1 | 9/2002 |
| EP | 1 275 309 A1 | 1/2003 |
| JP | 2004 075541 A | 3/2004 |
| WO | WO 99/63841 A1 | 12/1999 |
| WO | WO-00/41491 | 7/2000 |
| WO | WO 01/37681 A1 | 5/2001 |
| WO | WO 02/28204 A1 | 4/2002 |
| WO | WO 03/086108 A1 | 10/2003 |
| WO | WO 03/086468 A1 | 10/2003 |
| WO | WO 03/105611 A2 | 12/2003 |
| WO | WO 2005/074717 A1 | 8/2005 |
| WO | WO-2007/101464 | 9/2007 |

OTHER PUBLICATIONS

Nguyen T T: "The Cholesterol-Lowering Action of Plant Stanol Esters" Journal of Nutrition, Wistar Institute of Anatomy and Biology, Philadelphia, PA., US, vol. 129, No. 12, Dec. 1999, pp. 2109-2112, XP008007936.
Mensink R P et al.; "Effects of Plant Stanol Esters Supplied in Low-Fat Yoghurt on Serum Lipids and Lipoproteins; Non-Cholesterol Sterols and Fat Soluble Antioxidant Concentrations" Atherosclerosis, Amsterdam, NL, vol. 160, No. 1, Jan. 2002, pp. 205-213, XP001104063.
ISR in PCT/EP2006/011602, mailed May 3, 2007, 6 pgs.
PCT IPRP in PCT/EP2006/011602, issued Sep. 9, 2008, 6 pgs.
Non-Final Office Action in U.S. Appl. No. 12/282,169, dated Nov. 7, 2013, 15 pages.
Final Office Action in U.S. Appl. No. 12/282,169, dated Jul. 9, 2014, 15 pages.

\* cited by examiner

*Primary Examiner* — Michele L Jacobson
*Assistant Examiner* — Bhaskar Mukhopadhyay
(74) *Attorney, Agent, or Firm* — Servilla Whitney LLC

(57) ABSTRACT

Compositions in powder form of sterols or stanol esters, and milk powder and/or proteins are disclosed. A process of making the compositions is also disclosed. The suitability of incorporation of the compositions in powder form in food products, for example beverages and milk products, is also disclosed.

8 Claims, No Drawings

STEROL ESTER POWDER

CROSS REFERENCE TO RELATED APPLICATIONS

This application claims priority under 35 U.S.C. Section 119 of International Application No. PCT/EP2006/007997 filed Aug. 12, 2006 and German Patent Application No. 10 2005 039 836.7 filed Aug. 23, 2005, the contents of which are incorporated herein by reference in their entireties.

FIELD OF THE INVENTION

This invention relates generally to foods and, more particularly, to compositions containing sterol and/or stanol esters for incorporation in foods, cosmetic and pharmaceutical preparations, to a process for their production and to preparations, more particularly foods, which contain these compositions.

BACKGROUND OF THE INVENTION

The addition of sterols and stanols to foods for their cholesterol-lowering properties and the resulting prevention of future diseases, such as atherosclerosis, heart disease and hypertension, has been known for years.

Since phytosterols and stanols are insoluble in water and only poorly soluble in fats and oils, the incorporation of these cholesterol-lowering agents in food preparations, cosmetic or pharmaceutical products poses considerable problems. The unfavorable solubility behavior of the substances results not only in poor dispersibility, but also in reduced bioavailability and in unsatisfactory stability of the food preparations. Accordingly, the prior art proposes numerous formulations for solving these problems.

Efforts to increase solubility included the formulation of esters of the sterols, as described, for example, in European patent application EP 1275309 A1, or esters of the stanols, as described in U.S. Pat. No. 5,502,045, which had slightly improved processability, but which also showed lower hypocholesterolaemic activity in relation to the free sterols. However, the esterified derivatives also show insufficient solubility to allow simple incorporation. Apart from the fact that the esterified sterols behave differently in their bioavailability, they also have other formulation properties through their different physicochemical character and necessitate the use of other auxiliaries.

Numerous patent applications describe how the availability of sterols can be improved by reducing their particle sizes, mainly by micronization. German Offenlegungsschrift DE 102 53 111 A1 describes powder-form phytosterol formulations with a mean particle size of 0.01 to 100 µm which can readily be redispersed in water. A process for the production of a sterol dispersion, in which the sterols have a particle size distribution of 0.1 to 30 µm, is disclosed in International patent application WO 03/105611 A2.

However, the micronization of the sterol particles is often not in itself sufficient to enable good incorporation to be achieved. Although the bioavailability of the finely dispersed particles can be improved by increasing the surface, the micronized particles show poor wetting behavior, readily aggregate and generally float on water-containing surfaces. In many cases, the ground sterol can only be dispersed in a beverage by special methods involving intensive mixing. However, intensive mixers are not normally available to the end user of the food manufacturers.

Accordingly, many manufacturers combine micronization of the sterols with the additional use of emulsifiers. One example of this are the preparations described in European patent EP 0897671 B1 which contain sterols and sterol esters with a particle size of at most 15 µm in a mixture with selected emulsifiers, the ratio by weight of emulsifier to sterol in the aqueous phase being less than 1:2. A particular disadvantage of these known preparations is that they tend to agglomerate.

Emulsifiers commonly used in foods are monoglycerides and polysorbates (U.S. Pat. No. 6,623,780 B1, U.S. Pat. No. 6,376,482 B2, WO 02/28204 A1). Powder-form sterol ester formulations having a low protein content and also containing mono- and diglycerides as emulsifiers are disclosed in International patent application WO 03/086468 A1. Even though these emulsifiers are distinguished by high compatibility and have been known for some time as food emulsifiers, efforts are being made to reduce the quantity in which such emulsifiers are used or even to avoid them altogether because emulsifiers also influence the bioavailability of other substances present in the foods or can adversely affect the stability of the formulations. Avoiding emulsifiers was also the goal of the sterol formulations disclosed in European patent EP 1059851 B1 which contain thickeners for better dispersibility. However, these preparations are not sufficiently stable.

Numerous other methods for improving solubility and dispersibility, such as formulation as emulsions, microemulsions, dispersions, suspensions or complexing with cyclodextrins or bile salts, are described in International patent application WO 99/63841 A1, which also mentions formulation in the form of preparations. PEG, PVP, copolymers, cellulose ethers and esters are proposed as carriers. The direct use of food bases as carriers for powdered sterols is also known, cf. EP 1 003 388 B1.

The choice of proteins as carriers for unesterified sterols and stanols is disclosed in WO 01/37681. Synergistic effects of sitosterol and soya proteins are described in EP 0669835 B1.

The problem addressed by the present invention was to provide compositions which would be free from the disadvantages described above and which would enable sterol and/or stanol esters to be simply and effectively dispersed in foods without any need for emulsifiers, more particularly such emulsifiers as lecithins, monoglycerides, diglycerides, polysorbates, sodium stearyl lactate, glycerol monostearate, lactic acid esters and polyglycerol esters. In addition, the sterol and/or sterol ester compositions would be simple to produce and would be distinguished over prior art compositions by good storage stability.

BRIEF SUMMARY OF THE INVENTION

The present invention provides a composition in powder form which comprises:
(a) about 50 to 90% by weight of an ester of a sterol and/or a stanol;
(b) about 5 to 50% by weight milk powder and/or a protein, based on the total weight of the composition; and
with the proviso that no emulsifiers other than those of component (b) are present.

Another aspect of the present invention is directed to a process for the production of a sterol and/or stanol ester composition in powder form, which process comprises,
(i) dispersing or dissolving milk powder or a protein (component (b)), optionally together with an antioxidant and/or or a carbohydrate (component (c)), in water at room temperature to form a dispersion or a solution;

(ii) heating the dispersion or solution to a temperature of about 50 to 90° C.;
(iii) adding the ester of a sterol and/or stanol (component (a)) also heated to a temperature of about 50 to 90° C. to the heated dispersion;
(iv) homogenizing components (a), (b) and optionally (c) to form an emulsion; and
(v) spray drying the emulsion to produce the sterol and/or stanol ester composition in powder form.

Yet another aspect of the invention is a food product, for example a beverage or a milk product, which comprises from about 0.1% to about 50% by weight of the composition of the invention.

By virtue of the presence of milk powder or proteins, especially emulsifiers of the caseinate type, the compositions according to the invention are distinguished by good solubilizing properties, reduced aggregation and agglomeration properties and improved wettability, thus allowing the simple dispersion of sterol and stanol esters in water- and fat-containing preparations. The compositions possess excellent handling properties since they can be further processed without expensive machinery and, in addition, exhibit excellent long-term stability. They thus provide advantages over preparations which either are completely free from emulsifiers or contain such emulsifiers as lecithins, monoglycerides, diglycerides, polysorbates, sodium stearyl lactylate, glycerol monostearate, lactic acid esters and polyglycerol esters.

The compositions according to the invention may readily be incorporated in foods, more particularly in milk, milk beverages, whey and yoghurt beverages, margarine, fruit juices, fruit juice mixtures, fruit juice beverages, vegetable juices, carbonated and still beverages, soya milk beverages or high-protein liquid food substitute beverages and fermented milk preparations, yoghurt, drinking yoghurt or cheese preparations, and in cosmetic or pharmaceutical preparations.

The proviso "free from other emulsifiers than those of group (b)" shall be understood to mean that the use in particular of typical food emulsifiers, such as lecithins, monoglycerides, diglycerides, polysorbates, sodium stearyl lactylate, glycerol monostearate, lactic acid esters and polyglycerol esters, is avoided for the reasons described above. Although emulsifiers naturally occurring in foods, such as cholesterol, for example, cannot be avoided in the pre-formulation; no other emulsifiers are intended to be added as auxiliaries during the production of the sterol/stanol preparations according to the invention.

DETAILED DESCRIPTION OF THE INVENTION

Other than in the operating examples, or where otherwise indicated, all numbers expressing quantities of ingredients or reaction conditions used herein are to be understood as modified in all instances by the term "about."

The use of "and/or" shall be understood that, for example, "A and/or B" shall encompass the following embodiments: "A" or "B" or "A and B."

It shall be also understood that "tester" shall encompass one or more esters; "sterol" shall encompass one or more sterols; and "stanol" shall encompass one or more stanols, as well as mixtures thereof.

It shall be further understood that the use of the singular as used herein shall encompass one or more of the components described. The use of the plural herein shall be understood to encompass the singular as well as the plural form.

Sterols and/or Stanol Esters

Esters of sterols obtained from plants and vegetable raw materials, so-called phytosterols and phytostanols, are used for the purposes of the invention. Known examples are ergosterol, brassica sterol, campesterol, avenasterol, desmosterol, clionasterol, stigmasterol, poriferasterol, chalinosterol, sitosterol and mixtures thereof. Of these, β-sitosterol and campesterol are preferably used. The hydrogenated saturated forms of the sterols, so-called stanols, are also included among the compounds used, β-sitostanol and campestanol esters again being preferred. Vegetable raw material sources include, inter alia, seeds and oils of soybeans, canola, palm kernels, corn, cocoa, rape, sugar cane, sunflower, olive, cotton, soya, peanut or products from tall oil production. Esterification products with saturated and/or unsaturated $C_{6-22}$ and preferably $C_{12-18}$ fatty acids are preferably processed, although the invention is not limited to esters of this type. Phenolic acid esters, more particularly derivatives of cinnamic acid, caffeic acid and ferulic acid, may also be used. Naturally occurring esters may be directly obtained from vegetable raw materials or the sterol/stanol esters may be produced by transesterification with other esters. Derivatives obtained by esterification of free sterols or stanols with the corresponding fatty acids may also be used. The preparations according to the invention contain 50 to 90% by weight, preferably 60 to 80% by weight and more particularly 62 to 76% by weight sterol and/or stanol esters, based on the powder-form compositions.

Accordingly, the present invention also relates to food preparations containing sterol/stanol ester formulations having the above-mentioned composition. They are preferably used in beverages and milk products which contain 0.1 to 50% by weight and preferably 1 to 20% by weight of the powder-form preparations, based on the total weight of the foods.

Milk Powders and/or Proteins

Commercially available whole milk and skimmed milk powders obtained from the particular milk products by drying are used as the milk powder. They may be used in the form of mixtures with other proteins or as sole carrier. If other proteins are added or if proteins rather than the milk powder are used as the carrier, the proteins in question are understood to be isolated proteins which are obtained from natural animal and vegetable sources and which are added in the production of the powder-form preparations. Possible sources for proteins are plants, such as wheat, soya, lupins, corn, or sources of animal origin, such as eggs or milk.

Milk powder or proteins obtained from milk, such as sodium and/or calcium caseinates, are preferably used. Caseinates are particularly preferred for the purposes of the invention because, on the one hand, they have emulsifying properties without, at the same time, showing the above-mentioned disadvantages of the food emulsifiers otherwise typically used in particular for the production of beverages and milk products, more especially fermentation products, such as yoghurt. Caseinates, and particularly sodium or calcium caseinates, are otherwise typically used as emulsifiers in the manufacture of meat and sausage products.

The compositions according to the invention contain about 5 to 50% by weight, preferably about 10 to 30% by weight, more preferably about 12 to 20% by weight and most preferably about 12 to 15% by weight milk powder and/or proteins, based on the emulsifier-free powder-form preparation. Sodium caseinate and/or calcium caseinate are preferably used as the proteins.

Carbohydrates

An additional improvement in dispersibility, which affords advantages in particular in the incorporation of sterol ester powders in clear liquids, was achieved by the addition of carbohydrates. The compounds used as carbohydrates all contain food-grade sugars selected from the group consisting of glucose, sucrose, fructose, trehalose, maltose, maltodextrin, cyclodextrin, invert sugar, palatinose and lactose, and mixtures thereof. Glucose in the form of glucose syrup is preferably used as the carbohydrate. The use of about 3 to 30% by weight, preferably about 5 to 20% by weight and, more particularly, about 10 to 20% by weight carbohydrates, based on the weight of the powder-form sterol/stanol ester formulation, has proved beneficial to the dispersibility and stability of the preparation.

Compositions in which the ratio by weight of milk powder and/or protein—component b)—to the carbohydrates—component c)—is about 1:5 to 5:1, preferably about 1:3 to 3:1 and, more particularly, about 1:1 to 1:1.5, are particularly advantageous in regard to enhancing the formulation of the compositions of the present invention.

Other Auxiliaries

The compositions according to the invention may contain antioxidants, preservatives and flow promoters as further auxiliaries. Examples of possible antioxidants or preservatives are tocopherols, lecithins, ascorbic acid, parabens, butyl hydroxytoluene, anisole, or benzoic acid and salts thereof. Tocopherols are preferably used as antioxidants Silicon dioxide is preferably used as a flow regulator and promoter.

Production

The present invention also relates to a process for the production of the powder-form sterol and/or stanol ester compositions, which process comprises:
(i) dispersing or dissolving milk powder and/or proteins (component b), optionally together with antioxidants and/or carbohydrates (component c), in water at room temperature and heating the dispersion or solution to a temperature of about 50 to 90° C. to form a heated dispersion or solution;
(ii) adding the esters of sterols and/or stanols (component a) also heated to a temperature of 50 to 90° C. to the heated dispersion or solution; and homogenizing the components to form an emulsion; and
(iii) spray drying the emulsion formed to produce the sterol and/or stanol ester composition in powder form.

The emulsifier-free powder-form compositions are preferably obtained by:
(i) dispersing or dissolving the milk powder and/or proteins (component b), optionally together with antioxidants and/or carbohydrates (component c), in water at room temperature and heating the dispersion or solution to a temperature of about 60 to 80° C. to form a heated dispersion or solution,
(ii) adding the esters of sterols and/or stanols (component a) also heated to a temperature of 60 to 80° C. to the heated dispersion or solution; and homogenizing the components to form an emulsion; and
(iii) finely dispersing the emulsion formed through a rotating disk and subjecting the dispersed emulsion to spray drying.

Powder-Form Compositions

Compositions according to the invention are (all quantities based on the total weight of the particular preparation):
(A) Powder-form compositions containing
　(a) 50 to 90% by weight esters of sterols and/or stanols and
　(b) 5 to 50% by weight milk powder.
(B) Powder-form compositions containing
　(a) 50 to 90% by weight fatty acid esters of sterols and/or stanols and
　(b) 10 to 30% by weight milk powder and/or proteins.

The following formulations are preferred for their improved storage stability, dispersibility and processability in foods:

(C) Powder-form compositions containing
　(a) 60 to 80% by weight fatty acid esters of sterols and/or stands and
　(b) 5 to 50% by weight milk powder and/or proteins.
(D) Powder-form compositions containing
　(a) 50 to 90% by weight fatty acid esters of sterols and/or stanols,
　(b) 5 to 50% by weight milk powder and/or proteins and
　(c) 3 to 30% by weight carbohydrates.

Compositions having the following composition are particularly preferred:
(E) Powder-form compositions containing
　(a) 60 to 80% by weight fatty acid esters of sterols and/or stanols and
　(b) 10 to 30% by weight milk powder and/or sodium and/or calcium caseinate.
(F) Powder-form compositions containing
　(a) 60 to 80% by weight fatty acid esters of sterols and/or stanols,
　(b) 12 to 20% by weight milk powder and/or proteins and
　(c) 5 to 20% by weight carbohydrates.
(G) Powder-form compositions containing
　(a) 60 to 80% by weight fatty acid esters of sterols and/or stanols,
　(b) 10 to 30% by weight milk powder and/or sodium and/or calcium caseinate and
　(c) 10 to 20% by weight carbohydrates.

Emulsions having the following composition are especially preferred:
(H) Powder-form compositions containing
　(a) 62 to 76% by weight fatty acid esters of sterols and/or stanols and
　(b) 10 to 30% by weight milk powder and/or sodium and/or calcium caseinate.
(I) Powder-form compositions containing
　(a) 60 to 80% by weight fatty acid esters of sterols and/or stanols,
　(b) 5 to 50% by weight sodium and/or calcium caseinate and
　(c) 10 to 20% by weight glucose.
(J) Powder-form compositions containing
　(a) 60 to 80% by weight fatty acid esters of sterols and/or stanols,
　(b) 10 to 30% by weight sodium and/or calcium caseinate and
　(c) 3 to 30% by weight glucose.

Formulations with the following composition have the best storage stability:
(K) Powder-form compositions containing
　(a) 62 to 76% by weight fatty acid esters of sterols and/or stanols,
　(b) 12 to 15% by weight sodium and/or calcium caseinate and
　(c) 10 to 20% by weight glucose.

The following examples are for the purpose of illustrating the invention and should not be construed in any manner whatsoever as limiting the scope of the present invention.

EXAMPLES

Example 1

29.5 g spray dried skimmed milk powder (Almil), 0.5 g tetrapotassium pyrophosphate (Budenheim) and 0.05 g sodium ascorbate (Rewe) were dispersed in 170 grams of water. The dispersion was heated to about 70° C. 70 grams of sterol ester (Vegapure® 95 E, Cognis Deutschland GmbH)

were heated to about 70° C. and added with stirring to the aqueous dispersion. The pH value of the dispersion was between 6.8 and 7.4. The pre-emulsion thus prepared was then homogenized at 220/30 bar in a Schröder LAB 100/60 homogenizer (about three passes in succession), the temperature of the emulsion being maintained at 65 to 70° C. Finally, the emulsion thus prepared was spray dried under the following conditions in an APV type LAB 3S spray drying tower:

| | |
|---|---|
| dry matter | about 45% |
| inflowing air temperature | 180° C. |
| exhaust air temperature | 90 ± 5° C. |
| atomizer speed | 24000 rpm |
| fluidized bed | |
| inflowing air temp., section ½ | 30-35° C. |
| inflowing air temp., section 3 | 4 to 8° C. |
| rotating sieve | 1 mm |

In a mixer (Gericke), 1% $SiO_2$ was added as a flow aid. The powder thus produced was distinguished by good stirrability at room temperature both in water and in milk (0.3 and 1.5% by weight fat content).

Example 2

14.8 g casein (Almil) were dispersed in 75 g water and, after the addition of about 9 grams of 20% sodium hydroxide, the dispersion was heated to 80° C. and stirred until a clear solution with a pH value of about 7 was formed. 12 grams of glucose syrup (80%) and 0.05 g sodium ascorbate (Rewe) were then dispersed in 100 grams water. The dispersion was heated to about 70° C. and added to the sodium caseinate solution. 71 grams of sterol ester (Vegapure® 95 E, Cognis Deutschland GmbH) were heated to about 70° C. and added with stirring to the aqueous dispersion. The pH value of the dispersion was between 6.8 and 7.4. The pre-emulsion thus prepared was then homogenized at 220/30 bar in a Schröder LAB 100/60 homogenizer (about three passes in succession), the temperature of the emulsion being maintained at 65 to 70° C. Finally, the emulsion thus prepared was spray dried in an APV type LAB 3S spray drying tower under the same conditions as in Example 1.

The invention claimed is:

1. A process for the production of a storage stable sterol ester and/or a stanol ester composition in powder form, said process comprising the steps of:
   (i) dispersing or dissolving about 12 to about 15% by weight of sodium and/or calcium caseinate (component (b)), and about 10 to about 20% by weight of glucose (component (c)), optionally together with an antioxidant, in water at room temperature to form a dispersion or a solution;
   (ii) heating said dispersion or solution to a temperature of about 50 to about 90° C.;
   (iii) adding about 62 to about 76% by weight of a fatty acid ester of a sterol and/or a fatty acid ester of a stanol (component (a)), also heated to a temperature of about 50 to about 90° C., to the heated dispersion;
   (iv) homogenizing the heated dispersion comprising components (a), (b), (c) and optional antioxidant, to form an emulsion; and
   (v) spray drying said emulsion to produce the sterol ester and/or stanol ester composition in powder form,
   with the proviso that no emulsifiers other than those of component (b) are present.

2. The process of claim 1, wherein the dispersion or solution is heated to a temperature of about 60 to 80° C. in step (ii).

3. The process of claim 1, wherein the ester of a sterol and/or ester of a stanol is heated to a temperature of about 60 to 80° C.

4. The process of claim 1, wherein the emulsion is dispersed through a rotating disk prior to spray drying.

5. The process of claim 1 further comprising incorporating the powder form composition in a food preparation.

6. The process of claim 5, wherein the powder form composition is incorporated in milk, yogurt, margarine, fruit juice, vegetable juice, or cheese.

7. The process of claim 5, wherein the powder form composition is incorporated in the food preparation in an amount of 0.1-50% based on total weight of the food preparation.

8. The process of claim 7, wherein the powder form composition is incorporated in the food preparation in an amount of 1-20% based on total weight of the food preparation.

* * * * *